US00PP33568P2

(12) United States Plant Patent
Wood

(10) Patent No.: US PP33,568 P2
(45) Date of Patent: Oct. 19, 2021

(54) ***HIBISCUS* PLANT NAMED 'SMNHSPCL'**

(50) Latin Name: *Hibiscus syriacus*
Varietal Denomination: SMNHSPCL

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 17/039,932

(22) Filed: Sep. 30, 2020

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
See application file for complete search history.

*Primary Examiner* — Annette H Para
(74) *Attorney, Agent, or Firm* — C. Anne Whealy

(57) ABSTRACT

A new and distinct cultivar of *Hibiscus* plant named 'SMNHSPCL', characterized by its upright to outwardly spreading and arching plant habit; moderately vigorous growth habit; large and full semi-double flowers with purple-colored petals and petaloids with purplish red-colored centers and venation; relatively long flowering period; and good garden performance.

2 Drawing Sheets

Figure 1:
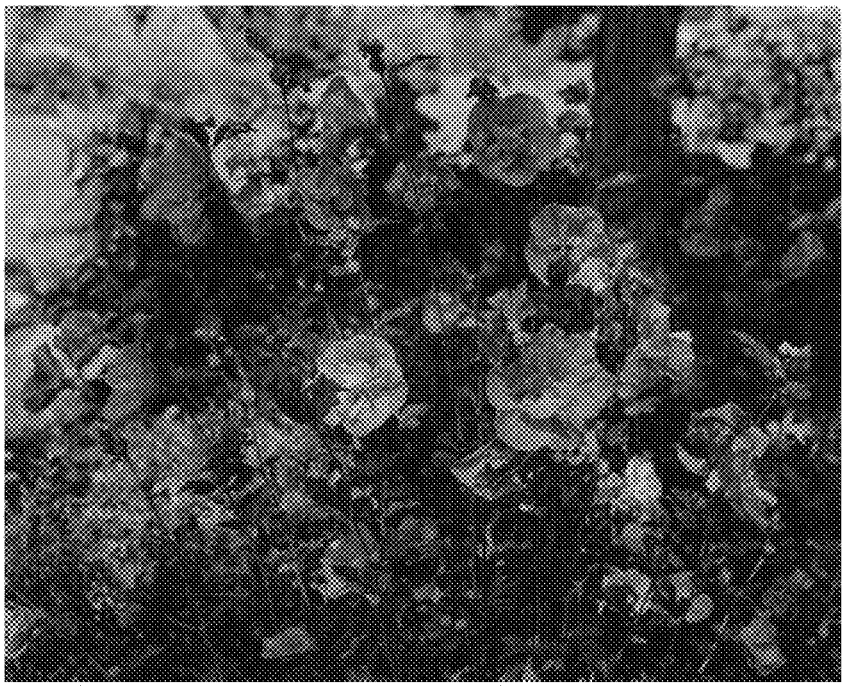

Botanical designation: *Hibiscus syriacus.*
Cultivar denomination: 'SMNHSPCL'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Hibiscus* plant, botanically known as *Hibiscus syriacus*, commercially and commonly known as Rose-of-Sharon or Althea, and hereinafter referred to by the cultivar name 'SMNHSPCL'.

The new *Hibiscus* plant is a product of a planned breeding program conducted by the Inventor in Grand Haven, Mich. The objective of the breeding program was to develop new *Hibiscus* plants with attractive flower forms and colors.

The new *Hibiscus* plant originated from an open-pollination during the summer of 2015 of *Hibiscus syriacus* 'Notwoodone', not patented, as the female, or seed, parent with an unknown selection of *Hibiscus syriacus* as the male, or pollen, parent. The new *Hibiscus* plant was discovered and selected by the Inventor during the summer of 2015 as a single flowering plant from within the progeny of the stated open-pollination in a controlled environment in Grand Haven, Mich.

Asexual reproduction of the new *Hibiscus* plant by softwood cuttings since the summer of 2015 in a controlled environment in Grand Haven, Mich. has shown that the unique features of this new *Hibiscus* plant are stable and reproduced true to type in successive generations of asexual reproduction.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNHSPCL'. These characteristics in combination distinguish 'SMNHSPCL' as a new and distinct *Hibiscus* plant:

1. Upright to outwardly spreading and arching plant habit.
2. Moderately vigorous growth habit.
3. Large and full semi-double flowers with purple-colored petals and petaloids with purplish red-colored centers and venation.
4. Relatively long flowering period.
5. Good garden performance.

Plants of the new *Hibiscus* can be compared to plants of the female parent, 'Notwoodone'. Plants of the new *Hibiscus* differ primarily from plants of 'Notwoodone' in flower color as flowers of plants of the new *Hibiscus* have purple-colored petals and petaloids whereas flowers of plants of 'Notwoodone' have light violet-colored petals and petaloids. In addition, flowers of plants of the new *Hibiscus* have more petaloids than flowers of plants of 'Notwoodone'.

Plants of the new *Hibiscus* can be compared to plants of the *Hibiscus syriacus* 'Rwoods5', disclosed in U.S. Plant Pat. No. 29,683. In side-by-side comparisons, plants of the new *Hibiscus* differ from plants of 'Rwoods5' in the following characteristics:

1. Plants of the new *Hibiscus* are more outwardly spreading than and not as upright as plants of 'Rwoods5'.
2. Plants of the new *Hibiscus* are more freely branching than plants of 'Rwoods5'.
3. Plants of the new *Hibiscus* and 'Rwoods5' differ in flower color as flowers of plants of the new *Hibiscus* have purple-colored petals and petaloids whereas flowers of plants of 'Rwoods5' have purplish pink-colored petals and petaloids.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet (FIG. 1) is a side perspective view of a typical plant of 'SMNHSPCL' grown in an outdoor nursery.

Figure 2:
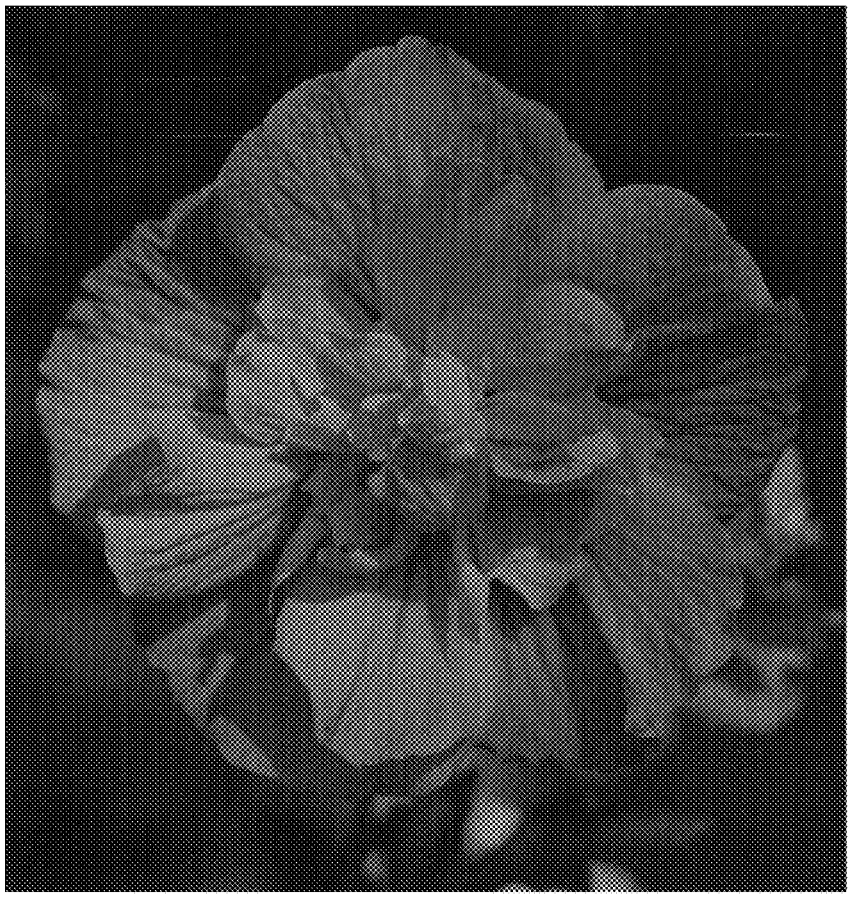

The photograph on the second sheet (FIG. 2) is a close-up view of a typical flower of 'SMNHSPCL'.

DETAILED BOTANICAL DESCRIPTION

The following observations, measurements and values describe plants grown in three-gallon containers during the summer in a polypropylene-covered shadehouse in Grand Haven, Mich. and under cultural practices typical of commercial *Hibiscus* production. During the production of the plants, day temperatures ranged from 18° C. to 27° C. and night temperatures ranged from ranged from 5° C. to 10° C. Plants were two years old when the photographs and the description were taken. In the following detailed description, color references are made to The Royal Horticultural Society Colour Chart, 2015 Edition, except where general terms of ordinary dictionary significance are used.

Botanical classification: *Hibiscus syriacus* 'SMNHSPCL'.

Parentage:

*Female, or seed, parent.*—*Hibiscus syriacus* 'Notwoodone', disclosed in U.S. Plant Pat. No. 12,619.

*Male, or pollen, parent.*—Unknown selection of *Hibiscus syriacus*, not patented.

Propagation:

*Type.*—By softwood cuttings.

*Time to initiate roots, summer.*—About 20 days at temperatures about 18° C. to 27° C.

*Time to produce a rooted young plant, summer.*—About three months at temperatures about 18° C. to 27C.

*Root description.*—Medium in thickness, fibrous; typically tan to brown in color, actual color of the roots is dependent on substrate composition, water quality, fertilizer, substrate temperature and physiological age of roots.

*Rooting habit.*—Moderately freely branching; medium density.

Plant description:

*Plant and growth habit.*—Perennial shrub; upright to outwardly spreading and arching plant habit; moderately vigorous growth habit and moderate growth rate.

*Branching habit.*—Freely branching habit, usually about 50 to 75 lateral branches develop per plant; pinching enhances lateral branch development.

*Plant height.*—About 88 cm.

*Plant diameter* (*area of spread*).—About 102 cm.

Lateral branch description:

*Length.*—About 60 cm.

*Diameter.*—About 3 mm to 4 mm.

*Internode length.*—About 5 cm to 7 cm.

*Aspect.*—Erect to about 35° from vertical.

*Strength.*—Moderately strong.

*Texture.*—Woody, glabrous.

*Color.*—Close to 197C.

Leaf description:

*Arrangement.*—Alternate, simple.

*Length.*—About 6.25 cm.

*Width.*—About 3.75 cm.

*Shape.*—Lobed, roughly rhomboidal.

*Apex.*—Acute.

*Base.*—Cuneate.

*Margin.*—Lobed; undulate.

*Texture, upper and lower surfaces.*—Coriaceous with distinct venation; mostly glabrous with sparse pubescence along the midvein.

*Venation pattern.*—Palmate.

*Color.*—Developing and fully expanded leaves, upper surface: Close to NN137B; venation, close to 138B. Developing and fully expanded leaves, lower surface: Close to 147B; venation, close to 145C.

*Petioles.*—Length: About 1.25 cm. Diameter: About 2 mm. Texture, upper surface: Pubescent. Texture, lower surface: Smooth, glabrous. Color, upper surface: Close to 144A. Color, lower surface: Close to N144C.

Flower description:

*Flower appearance and arrangement.*—Relatively large semi-double rotate flowers; flowers mostly terminal; freely flowering habit with usually about 50 flowers developing per plant; flowers face upright to outwardly.

*Flower longevity.*—Flowers last several days on the plant; flowers not persistent.

*Natural flowering season.*—Plants of the new *Hibiscus* flower continuously during the summer in Michigan.

*Flower diameter.*—About 9 cm.

*Flower length* (*height*).—About 4.5 cm.

*Flower buds.*—Length: About 2 cm to 3.5 cm. Diameter: About 1 cm to 2 cm. Shape: Ovoid. Color: Close to N81B.

*Petals.*—Arrangement and quantity: Single whorl of six petals; petals imbricate. Length: About 4.5 cm to 5 cm. Width: About 3.5 cm to 4 cm. Shape: Broadly obovate. Apex: Obtuse. Base: Attenuate. Margin: Entire; undulate. Texture, upper and lower surfaces: Smooth, glabrous; satiny, delicate. Color: When opening and fully opened, upper surface: Close to 84A; towards the base, close to 61B; venation, close to 84A and 61B; color does not change with development. When opening and fully opened, lower surface: Close to N82C; towards the margins, close to NN155D; towards the base, close to 61B to 61C; venation, close to N82C, NN155D, 61B and 61C; color does not change with development.

*Petaloids*.—Arrangement and quantity: About 50 massed in the center of the flower giving a ruffled appearance; petaloids imbricate. Length: About 1 cm to 3 cm. Width: About 4 mm to 8 mm. Shape: Oblanceolate. Apex: Obtuse. Base: Attenuate. Margin: Entire. Texture, upper and lower surfaces: Smooth, glabrous; satiny, delicate. Color: When opening and fully opened, upper surface: Close to N75B; towards the base, close to NN155D; venation, close to N75B, 61B and NN155D; color does not change with development. When opening and fully opened, lower surface: Close to a mixture of 76D and NN155D; venation, close to 76D and NN155D; color does not change with development.

*Calyx*.—Arrangement and quantity: Single whorl of four or five sepals fused into a tubular calyx. Sepal length: About 1 cm. Sepal width: About 8 mm. Sepal shape: Deltoid. Sepal apex: Acute. Sepal base: Truncate. Sepal margin: Entire. Sepal texture, upper surface: Rough, glabrous. Sepal texture, lower surface: Smooth, glabrous. Sepal color, upper and lower surfaces: Close to 144C.

*Epicalyx*.—Arrangement and quantity: Single whorl of six to eight sepals fused into a tubular epicalyx. Sepal length: About 1.3 cm. Sepal width: About 1 mm. Sepal shape: Acicular. Sepal apex: Acute. Sepal base: Truncate. Sepal margin: Entire. Sepal texture, upper surface: Rough, glabrous. Sepal texture, lower surface: Smooth, glabrous. Sepal color, upper surface: Close to 144B. Sepal color, lower surface: Close to 141B.

*Peduncles*.—Length: About 8 mm. Diameter: About 4 mm. Aspect: About 45° from stein axis. Strength: Strong. Texture: Pubescent. Color: Close to N144D.

*Reproductive organs*.—Androecium: Quantity of stamens per flower: About 16. Filament length: About 7 mm. Filament color: Close to 157D. Anther shape: Round. Anther length: About 2 mm. Anther color: Close to 157D. Amount of pollen: Moderate. Pollen color: Close to 157D. Gynoecium: Quantity of pistils per flower: Six. Pistil length: About 2 cm. Style length: About 1.7 cm. Style color: Close to 157D. Stigma appearance: Peltate. Stigma color: Close to 157D. Seeds and fruits: To date, seed and fruit development have not been observed on plants of the new *Hibiscus*.

Garden performance: Plants of the new *Hibiscus* have been observed to have excellent garden performance and to tolerate rain, wind, drought and temperatures ranging from about −32° C. to about 36° C.

Pathogen & pest resistance: To date, plants of the new *Hibiscus* have not been shown to be resistant to pathogens and pests common to *Hibiscus* plants.

It is claimed:

1. A new and distinct *Hibiscus* plant named 'SMNHSPCL' as illustrated and described.

* * * * *